United States Patent [19]

Ichiriki et al.

[11] Patent Number: 4,950,742

[45] Date of Patent: Aug. 21, 1990

[54] PROCESS FOR PRODUCING AZOIMINO ETHERS BY OXIDATION OF HYDIAZONITRILES

[75] Inventors: Kazuo Ichiriki, Tokyo; Motoaki Tanaka, Urawa; Toru Okugawa, Sayama; Hiroyoshi Nawa, Fujimi, all of Japan

[73] Assignee: Wako Pure Chemical Industries, Ltd., Osaka, Japan

[21] Appl. No.: 318,525

[22] Filed: Mar. 6, 1989

Related U.S. Application Data

[63] Continuation of Ser. No. 939,844, Dec. 9, 1986, abandoned.

[30] Foreign Application Priority Data

Jan. 14, 1986 [JP] Japan .................................. 61-6092

[51] Int. Cl.$^5$ .................. C07C 245/02; C07C 251/02; C07C 251/08; C07C 251/12
[52] U.S. Cl. ................................. 534/738; 534/586; 534/838; 534/587
[58] Field of Search ................. 534/586, 587, 738, 838

[56] References Cited

U.S. PATENT DOCUMENTS

| | | | |
|---|---|---|---|
| 2,599,299 | 6/1952 | Upson | 534/738 |
| 3,775,395 | 11/1973 | Koyanagi et al. | 534/586 |
| 3,778,430 | 12/1973 | Citron | 534/586 X |
| 3,959,343 | 5/1976 | Arashi et al. | 534/586 X |
| 4,039,527 | 8/1977 | Nagaoka et al. | 534/586 X |

FOREIGN PATENT DOCUMENTS

| | | | |
|---|---|---|---|
| 0080275 | 6/1983 | European Pat. Off. | 534/586 |
| 2054248 | 4/1971 | France | 534/586 |
| 58-2230 | 1/1983 | Japan | 534/738 |
| 2111979 | 7/1983 | United Kingdom | 534/586 |

*Primary Examiner*—Floyd D. Higel
*Attorney, Agent, or Firm*—Armstrong, Nikaido, Marmelstein, Kubovcik & Murray

[57] ABSTRACT

An azoimino ether, which is an intermediate for preparing polymerization initiators, is prepared by reacting a hydrazonitrile having a hydrazo group and at least one cyano group in the molecule with chlorine in the presence of an alcohol, in a non-aqueous organic solvent.

5 Claims, No Drawings

PROCESS FOR PRODUCING AZOIMINO ETHERS BY OXIDATION OF HYDIAZONITRILES

This application is a continuation of application Ser. No. 939,840 filed Dec. 9, 1986, now abandoned.

BACKGROUND OF THE INVENTION

This invention relates to a process for producing azoimino ethers which are intermediates for the syntheses of azoguanyl compounds, azoamide compounds, azoester compounds and the like useful as polymerization initiators in the production of polymeric compounds.

Azoguanyl compounds are useful particularly as a polymerization initiator for use in aqueous solutions, because their mineral acid salts are water-soluble. Azoamide compounds are useful as polymerization initiator effectively usable in the non-salt form. Azoester compounds are useful as polymerization initiator excellent in solubility. Azoimino ethers are intermediates of these compounds useful as polymerization initiator. Hitherto, azoimino ethers have been produced by reacting the corresponding azonitrile compound in the presence of hydrogen chloride in an alcoholic solvent, as disclosed in U.S. Pat. No. 2,599,299. This process, however, is disadvantageous from the industrial point of view in that the progress of the reaction often becomes rapid and uncontrollable. On the other hand, as an improvement capable of solving the above-mentioned problem, the process mentioned in Japanese Patent Examined Publication No. 2,230/83 can be referred to. This process comprises reacting an azonitrile with an alcohol in the presence of hydrogen chloride gas in a solvent into which hydrogen chloride gas has a low solubility. According to this process, no rapid reaction takes place and the reaction is quite easy to control. Further, it is economical because it consumes only the approximately theoretical amount of hydrogen chloride. Thus, it can be said to be an industrially quite advantageous production process of azoimino ethers.

At any rate, however, these prior production processes of imino ethers which comprises reacting an azonitrile with an alcohol in the presence of hydrogen chloride gas (including the above-mentioned improvement) use expensive azonitrile and expensive hydrogen chloride gas as the starting materials, and therefore the produced imino ether is naturally expensive and there is a limitation in the cost down of the process. Accordingly, these processes cannot be said to be industrially satisfactory. Thus, it has been desired earnestly to develop a new industrial process capable of giving imino ethers less expensively.

SUMMARY OF THE INVENTION

An object of the invention is to overcome the above-mentioned disadvantages of the prior art processes and to provide an industrially quite practicable production process of azoimino ethers by which azoimino ethers can be produced less expensive than ever without any rapid reaction but with a very easily controllable reaction.

The present invention provides a process for producing an azoimino ether having an azo group (—N=N—) and at least one imino ether group

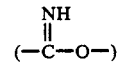

in its molecule which comprises reacting a hydrazonitrile having a hydrazo group

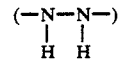

and at least one cyano group (—CN) in its molecule with chlorine in the presence of the an alcohol capable of converting the cyano group to an imino ether in the presence of hydrogen chloride.

DESCRIPTION OF THE PREFERRED EMBODIMENTS

In the prior processes, the starting azonitrile compound has been produced generally by the halogen oxidation of hydrazonitrile compound, and the hydrogen halide formed as by-product of the reaction has been disposed of because it is difficult to isolate. However, this is too wasteful. If the halogen oxidation of hydrazonitrile compound and the imino-etherification of azonitrile compound are carried out in one pot and one step, the cost of the process will be reduced owing to the simplification of process and effective utilization of by-product. Based on this expectation, the present inventors have conducted earnest studies to accomplish the present invention.

The hydrazonitrile used as a starting material in the invention has a hydrazo group

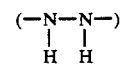

and at least one cyano group (—CN) in its molecule. Said hydrazonitrile may be any of symmetric hydrazonitrile and asymmetric hydrazonitrile. As examples of such hydrazonitriles, those of the following formula can be referred to:

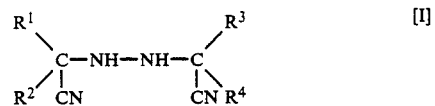

wherein $R^1$, $R^2$, $R^3$ and $R^4$ independently represent an alkyl group preferably having 1 to 5 carbon atoms; a substituted alkyl group such as hydroxyalkyl, alkoxyalkyl, haloalkyl and the like; a cycloalkyl group preferably having 3 to 6 carbon atoms; an aralkyl group such as benzyl, phenethyl and the like; a substituted aralkyl group having one or more alkyl groups, alkoxy groups, hydroxy groups, halogen atoms as its substituent; an aryl group such as phenyl, naphthyl, and the like; and a substituted aryl group having one or more alkyl groups, alkoxy groups, hydroxy groups, halogen atoms as its substituent; and at least one of combinations of $R^1$—$R^2$ and $R^3$—$R^4$ may form an aliphatic ring.

Concrete examples of said hydrazonitrile include 2,2'-hydrazobis(2-methylpropionitrile), 2,2'-hydrazobis(2-methylbutyronitrile), 2,2'-hydrazobis(2,4-dimethylvaleronitrile), 2,2'-hydrazobis(2-methylhexylonitrile), 2,2'-hydrazobis(2-cyclopropylpropionitrile), 2,2'-hydrazobis(2-phenylpropionitrile), 2-methyl-2-phenylhydrazinopropionitrile, 1,1'-hydrazobis(1-cyanocyclohexane), and the like.

As said alcohol capable of converting a cyano group (—CN) to an imino ether group in the presence of hydrogen chloride, primary alcohols having 1 to 4 carbon atoms such as methanol, ethanol, n-propanol, isopropanol, n-butanol and the like can be referred to, for example. Preferably, these alcohols are used in a nearly anhydrous state or in the state having as low a water content as possible. As for the amount of said alcohol, an amount ranging from the theoretical amount required for the iminoetherification to an amount 1.2 times as much as the theoretical amount is usually enough for the purpose.

As for the amount of the chlorine used in the invention, an amount ranging from the theoretical amount to a somewhat excessive amount is enough for the purpose.

The reaction temperature is somewhat dependent on the kind of azonitrile used. However, the reaction temperature is usually 10° C. to 40° C., preferably 20° C. to 35° C., and more preferably 25° C. to 30°.C.

The time of reaction is naturally dependent on the kind of azonitrile used and the reaction temperature adopted. If a reaction temperature of 25° C. to 30° C. is employed, the reaction time is usually about 4 to 24 hours.

According to the invention, hydrazo group

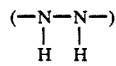

is converted to azo group (—N=N—) and cyano group (—CN) is converted to imino ether group

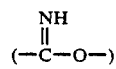

in one pot and one step.

The one-pot one-step reaction of the invention is usually carried out in a non-aqueous system in the presence of a solvent conventionally used in halogen oxidation and iminoetherification such as aromatic hydrocarbon (e.g. benzene, toluene and the like), halogenated hydrocarbon (e.g. dichloromethane, dichloroethane, chloroform, carbon tetrachloride and the like), and some others. That is to say, carrying out the reaction in a non-aqueous system is a preferable condition of the invention, and it is advisable to avoid the existence of water as possible.

The reaction of the invention itself is carried out under conditions capable of satisfying the conventional conditions of halogen oxidation and the conditions of iminoetherification. For example in the reaction of 2,2'-hydrazobis(2-methylpropionitrile), 2,2'-hydrazobis(2-methylpropionitrile) and an amount, ranging from the theoretical amount to 1.2 times the theoretical amount, of alcohol are added to the above-mentioned non-aqueous organic solvent, and an amount, ranging from the theoretical amount to a somewhat excessive amount, of chlorine gas is introduced thereinto at a temperature at which the reaction can progress effectively and the formed 2,2'-azobis(1-imino-1-methoxy-2-methylpropane) dihydrochloride does not decompose (usually 10° to 40° C., preferably 20° to 35° C., more preferably 25° to 30° C.). The introduction of chlorine gas is usually carried out while cooling and stirring the system. If a reaction temperature of, for example, 25° C. to 30° C. is employed, the reaction time is usually about 4 to 12 hours.

As the result of the reaction, the formed azoimino ether is obtained in the form of a HCl-addition salt thereof. If desired, the hydrogen chloride can be removed from the product by a usual procedure. The reaction product can be isolated and purified by a usual method.

The azoimino ether thus obtained is represented by the following formula:

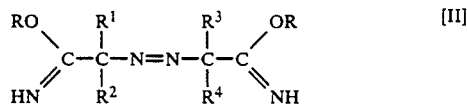

wherein $R^1$, $R^2$, $R^3$ and $R^4$ are as defined above; and R represents a lower alkyl group preferably having 1 to 4 carbon atoms.

According to the process of the invention, no rapid reaction takes place and the reaction is easy to control. The azoimino ether obtained is not inferior in yield and quality to that produced according to the prior art processes. The azoimino ether thus obtained is converted to a compound useful as polymerization initiator and the like. For example, it can be converted to a azoguanyl compound by reacting it with ammonia gas or an amine in an appropriate solvent. Otherwise, it can be converted to an azoester compound by hydrolysis. Otherwise, it can be converted to an azoamide compound by reacting the resulting azoester compound further with ammonia.

Referring to the following Examples, the invention will be illustrated in more detail.

EXAMPLE 1

To a mixture consisting of 111 ml of toluene and 11.5 g (0.36 mole) of methanol was added 24.9 g (0.15 mole) of 2,2'-hydrazobis(2-methylpropionitrile). While cooling and stirring the mixture, 11.2 g (0.158 mole) of chlorine gas was introduced thereinto at a temperature of 10° to 25° C. Then, the mixture was reacted at 25° to 30° C. for 5 hours and allowed to stand overnight. After the reaction, a crystalline precipitate was collected by filtration and dried to obtain 38.5 g of 2,2'-azobis(1-imino-1-methoxy-2-methylpropane).dihydrochloride melting at 124° C. (decomposition).

EXAMPLE 2

To 312 ml of carbon tetrachloride were added 19.2 g (0.60 mole) of methanol and 40 g (0.24 mole) of 2,2'-hydrazobis(2-methylpropionitrile). While stirring the solution, 18 g (0.51 mole) of chlorine gas was introduced thereto at a temperature of 20° to 25° C. with stirring. Subsequently, the resulting mixture was stirred and reacted first at 20° to 25° C. for six hours and then at 35° to 40° C. for one hour. After allowing the reaction mixture to stand overnight, crystals were collected by filtration and dried to obtain 66.5 g of 2,2'-azobis(1-imino-1-methoxy-2-methylpropane).dihydrochloride melting at 125° C. (decomposition).

As has been mentioned above, the present invention can provide a novel and very effective production process of azoimino ether which is the intermediate for the syntheses of azoguanyl compounds, azoamide compounds and azoester compounds useful as the polymerization initiator in the production of polymeric compounds. The process of the invention exhibits an outstanding effect in that it uses a hydrazonitrile compound, much less expensive than azonitrile compound, as its starting material and gives the corresponding azoimino ether from the hydrazonitrile compound in one pot and one step and in that it effectively utilizes the hydrogen halide formed as by-product when hydroazo group

is converted to azo group —N≡N— which makes the treatment of waste hydrogen halide unnecessary and thereby greatly reduces the cost to bring about a great merit to commerciallization.

What is claimed is:

1. A one-step, one-vessel process for producing an azoimino ether from a hydrazonitrile consisting essentially of reacting a hydrazonitrile with chlorine gas in the presence of a primary alcohol at a temperature of 10° to 40° C. and under anhydrous conditions in a non-aqueous solvent selected from the group consisting of aromatic hydrocarbons and halogenated hydrocarbons.

2. A process according to claim 1, wherein the alcohol is a primary alcohol having 1 to 4 carbon atoms.

3. A process according to claim 1 wherein the hydrazonitrile is represented by the formula:

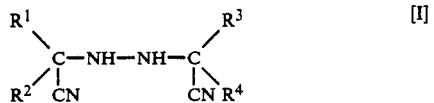

wherein $R^1$, $R^2$, $R^3$ and $R^4$ are independently a $C_{1-5}$ alkyl group; a substituted alkyl group, a $C_{3-6}$ cycloalkyl group, an aralkyl group, a substituted aralkyl group, an aryl group, or a substituted aryl group; and wherein at least one of the combinations of $R^1$—$R^2$ and $R^3$—$R^4$ may be joined by a carbon-carbon single bond.

4. A process according to claim 2, wherein the alcohol is methanol, ethanol, n-propanol, isopropanol, n-butanol, or a mixture thereof.

5. A process according to claim 1, wherein the non-aqueous solvent is benzene, toluene, dichloromethane, dichloroethane, chloroform, or carbon tetrachloride.

* * * * *